(12) United States Patent
Saxena et al.

(10) Patent No.: US 11,769,114 B2
(45) Date of Patent: Sep. 26, 2023

(54) COLLABORATION PLATFORM FOR ENABLING COLLABORATION ON DATA ANALYSIS ACROSS MULTIPLE DISPARATE DATABASES

(71) Applicant: Novartis AG, Basel (CH)

(72) Inventors: Sidhyansh Saxena, Basel (CH); Achim Plueckebaum, Basel (CH); Badhri Srinivasan, Basel (CH); Christian Diehl, Basel (CH)

( * ) Notice: Subject to any disclaimer, the term of this patent is extended or adjusted under 35 U.S.C. 154(b) by 0 days.

(21) Appl. No.: 17/541,441

(22) Filed: Dec. 3, 2021

(65) Prior Publication Data

US 2022/0180319 A1 Jun. 9, 2022

Related U.S. Application Data

(60) Provisional application No. 63/121,093, filed on Dec. 3, 2020.

(51) Int. Cl.
*G06Q 10/101* (2023.01)
*G16B 50/30* (2019.01)
(Continued)

(52) U.S. Cl.
CPC .......... *G06Q 10/101* (2013.01); *G16B 50/10* (2019.02); *G16B 50/20* (2019.02); *G16B 50/30* (2019.02); *G16H 80/00* (2018.01)

(58) Field of Classification Search
CPC ...... G06Q 10/101; G16B 50/10; G16B 50/20; G16B 50/30; G16H 80/00
See application file for complete search history.

(56) References Cited

U.S. PATENT DOCUMENTS 8,731,965 B2 5/2014 Erry et al.
9,830,475 B2 11/2017 Khandelwal
(Continued)

FOREIGN PATENT DOCUMENTS

CN 100452031 C 1/2009
CN 104573103 A 4/2015
(Continued)

OTHER PUBLICATIONS

Kurc, Tahsin, et al. "An XML-based system for synthesis of data from disparate databases." Journal of the American Medical Informatics Association 13.3 (2006): 289-301. (Year: 2006).*
(Continued)

*Primary Examiner* — Jesse P Frumkin
(74) *Attorney, Agent, or Firm* — Finnegan, Henderson, Farabow, Garrett & Dunner, LLP

(57) ABSTRACT

A platform and method for enabling collaboration on data analysis of life sciences data across disparate databases are disclosed. The collaboration platform may allow for performing exploratory analysis for drug discovery and development. The collaboration platform may include a search and graph module for generating a user project and determining and displaying one or more matching data assets and one or more potential collaborators; a collaboration module for coordinating a collaboration between the user and one or more selected collaborators; a data management module for receiving a schema for one or more producer projects, receiving data from the one or more selected data assets, and ingesting the received data using common standards and an ontology; and an insight application for generating disease specific inferences relating to a scientific question using the ingested received data, and receiving a feedback from the user and/or the selected collaborators to improve the search and graph module.

26 Claims, 8 Drawing Sheets

(51) Int. Cl.
*G16B 50/10* (2019.01)
*G16B 50/20* (2019.01)
*G16H 80/00* (2018.01)

(56) References Cited

U.S. PATENT DOCUMENTS

| | | |
|---|---|---|
| 2002/0029255 A1 | 3/2002 | Glynias et al. |
| 2008/0134140 A1 | 6/2008 | Weiner et al. |
| 2009/0281830 A1 | 11/2009 | McNames et al. |
| 2010/0174662 A1* | 7/2010 | Fabella, Jr. .......... G06Q 10/06 709/204 |
| 2010/0268551 A1 | 10/2010 | McNames et al. |
| 2011/0077959 A1 | 3/2011 | Klein |
| 2015/0032468 A1* | 1/2015 | Soon-Shiong ......... G16B 50/30 705/2 |
| 2015/0278451 A1 | 10/2015 | Kitano et al. |
| 2016/0004820 A1 | 1/2016 | Moore |
| 2017/0039327 A1 | 2/2017 | Bitran et al. |
| 2017/0039341 A1 | 2/2017 | Shklarski et al. |
| 2017/0076046 A1 | 3/2017 | Barnes et al. |
| 2017/0091686 A1* | 3/2017 | Goyal ................. G06Q 10/101 |
| 2017/0364538 A1 | 12/2017 | Jacob et al. |
| 2018/0089376 A1 | 3/2018 | Tucker et al. |
| 2018/0342323 A1* | 11/2018 | Shankar ................. G06N 5/022 |
| 2019/0108275 A1 | 4/2019 | Gull et al. |
| 2019/0171647 A1* | 6/2019 | Gaddipati ............. H04L 65/403 |
| 2019/0258950 A1 | 8/2019 | Birnbaum et al. |
| 2019/0272889 A1 | 9/2019 | Murray et al. |
| 2020/0058382 A1 | 2/2020 | Birnbaum et al. |
| 2020/0074118 A1 | 3/2020 | Sutton et al. |
| 2020/0176090 A1 | 6/2020 | Batra et al. |
| 2020/0176093 A1 | 6/2020 | Kuchibotla et al. |
| 2020/0234802 A1 | 7/2020 | Shelley et al. |
| 2020/0252767 A1 | 8/2020 | Reynolds et al. |
| 2020/0272919 A1 | 8/2020 | Haimson et al. |
| 2020/0294642 A1 | 9/2020 | Bostic et al. |
| 2020/0312457 A1 | 10/2020 | Kasthurirathne et al. |

FOREIGN PATENT DOCUMENTS

| | | |
|---|---|---|
| CN | 104866933 A | 8/2015 |
| CN | 106230800 A | 12/2016 |
| CN | 106777998 A | 5/2017 |
| CN | 107038671 A | 8/2017 |
| CN | 107169259 A | 9/2017 |
| CN | 111370106 A | 7/2020 |
| TW | 1467504 B | 1/2015 |
| TW | 1485638 B | 5/2015 |
| TW | 201837745 A | 10/2018 |
| WO | WO 2019/046854 A1 | 3/2019 |
| WO | WO 2019/097474 A1 | 5/2019 |
| WO | WO 2020/077352 A1 | 4/2020 |
| WO | WO 2020/081495 A1 | 4/2020 |
| WO | WO 2020/092316 A1 | 5/2020 |
| WO | WO 2020/117820 A1 | 6/2020 |
| WO | WO 2020/176476 A1 | 9/2020 |

OTHER PUBLICATIONS

Sahoo et al., Insight: An Ontology-based Integrated Database and Analysis Platform for Epilepsy Self-Management Research, Oct. 31, 2016; 94: 21-30, Int J Med Inform.
Jain et al., Ontology-Based Information Retrieval for Healthcare Systems, Jul. 10, 2020, Scrivener Publishing LLC.
International Search Report and Written Opinion from International Application No. PCT/US2021/061908 dated Apr. 4, 2022, 6 pages.
Office Action and Search Report from the Taiwanese Intellectual Property Office dated Sep. 27, 2022, in R.O.C. Application No. 110145232, 18 pages.
Office Action from the Taiwanese Intellectual Property Office dated Feb. 7, 2023, in counterpart R.O.C. Application No. 110145232, 16 pages.
Examination Notice from the Hong Kong Intellectual Property Office dated Mar. 20, 2023, in counterpart Hong Kong Application No. 22021043662.6, 9 pages.

* cited by examiner

COLLABORATION PLATFORM FOR ENABLING COLLABORATION ON DATA ANALYSIS ACROSS MULTIPLE DISPARATE DATABASES

RELATED APPLICATIONS

This application claims the benefit of priority to U.S. provisional Application No. 63/121,093, filed Dec. 3, 2020, which is incorporated herein by reference in its entirety.

BACKGROUND

Pharmaceutical companies have historically relied on the traditional model of clinical trials to find new molecules and develop new drugs. The current methods for performing research and development, however, are expensive and the time to develop new drugs have increased due to: (1) difficulty in finding novel breakthrough therapies; (2) increasing reliance on external assets for pipeline growth; (3) increasing cost of development, and (4) high failure rates, to name a few. Drug development for diseases that affect smaller segments of the population can be even more cost-prohibitive and, as a result, there is less incentive to develop treatments and drugs for these rare diseases. Moreover, traditional research and development methods also can take too long to find an effective treatment for many diseases.

Despite the vast amount of existing data, the scope of data that any one entity in the healthcare ecosystem is limited, siloed, and unstandardized. Each academic research institute or pharmaceutical or biotech company, for example, may have access only to its own trial and clinical research data, and these entities tend to be conducting research only in a few specialized areas. Hospitals, physicians, and health care record companies may have access to patient data but not clinical trial data. Other valuable data may be owned by lifestyle and digital health companies (like FitBit or Apple) or entities with DNA registries.

What is needed is a platform for leveraging the vast amounts of disease and treatment-related data and large databases that have already been developed by the healthcare ecosystem to optimize discovery and pre-clinical work. What is further needed are methods of standardizing and using large integrated data sets for in-silico drug delivery and analysis and ways to predict drug efficacy and response before going into trial. This will allow pharmaceutical and biotech companies to invest in assets that are most likely to succeed in trials and further achieve R&D savings. What is also needed is a collaborative system that enables entities to find and negotiate partnerships that may speed research and reduce costs. What is further needed are methods for designing better trials and protocols, identify better trial candidates, and produce more effective treatments and drugs. What is still further needed are methods and systems for precision medicine and better informing clinical decision making.

SUMMARY

One aspect of the present disclosure is directed to a collaboration platform for enabling collaboration on data analysis of life sciences data across multiple disparate databases. In at least one exemplary embodiment, the platform may be used for the solving of scientific questions using data, artificial intelligence (AI) models and insights from the disparate databases and systems. The platform may include a search and graph module for generating a user project. The user project may comprise multiple attributes determined from a) a user's profile; b) the user's past activities; c) system recommendations based on popularity; d) search terms, filters and/or indications of choices from one or more dropdown menus; and/or e) at least one scientific question in a natural language entered by the user. The search and graph module may be configured for determining and displaying one or more matching data assets, AI models, and/or one or more potential collaborators, wherein the matching data assets and potential collaborators are determined based on the user project and one or more producer projects, the one or more producer projects comprising one or more previously generated user projects. The platform may include a collaboration module for coordinating a collaboration between the user and one or more selected collaborators associated with one or more selected data assets selected by the user, the selected collaborators being a subset of the potential collaborators and the selected data assets being a subset of the matching data assets. Coordinating the collaboration may include notifying the selected collaborators associated with the one or more selected data assets; providing the selected collaborators with an abstract of the user project; providing the user with ability to inspect the one or more selected data assets; and finalizing the collaboration between the user and the selected collaborators, if the user and the one or more selected collaborators assent. The platform may include a data management module for receiving a schema for each of the one or more producer projects; receiving data from the one or more selected data assets; and ingesting the received data using common standards and an ontology. The platform may include an insight application for generating disease specific inferences relating to the scientific question using the ingested received data and receiving a feedback from the user and/or the selected collaborators to improve the search and graph module.

Another aspect of the disclosure is directed to a method for enabling collaboration on data analysis of life sciences data across multiple disparate databases. The method may allow for performing exploratory analysis for drug discovery and development. The method may include generating a user project, wherein the user project comprises multiple attributes determined from a) a user's profile; b) the user's past activities; c) system recommendations based on popularity; d) search terms, filters and/or indications of choices from one or more dropdown menus; and/or e) at least one scientific question in a natural language entered by the user. The method may include determining and displaying one or more matching data assets and one or more potential collaborators, wherein the matching data assets and potential collaborators are determined based on the user project and one or more producer projects, the one or more producer projects comprising one or more previously generated user projects. The method may include coordinating a collaboration between the user and one or more selected collaborators associated with one or more selected data assets selected by the user, the selected collaborators being a subset of the potential collaborators and the selected data assets being a subset of the matching data assets. The method may include notifying the selected collaborators associated with the one or more selected data assets. The method may include providing the selected collaborators with an abstract of the user project. The method may include providing the user with ability to inspect the one or more selected data assets. The method may include finalizing the collaboration between the user and the selected collaborators, if the user and the one or more selected collaborators assent. The method may include receiving a schema for each of the one or more producer projects; receiving data from the one or more selected data assets; and ingesting the received data using common standards and an ontology. The method may include generating disease specific inferences relating to the scientific question using the ingested received data; and receiving a feedback from the user and/or the selected collaborators to improve the search and graph module.

Other systems, methods, and computer-readable media are also discussed herein.

DETAILED DESCRIPTION

Figure 1:
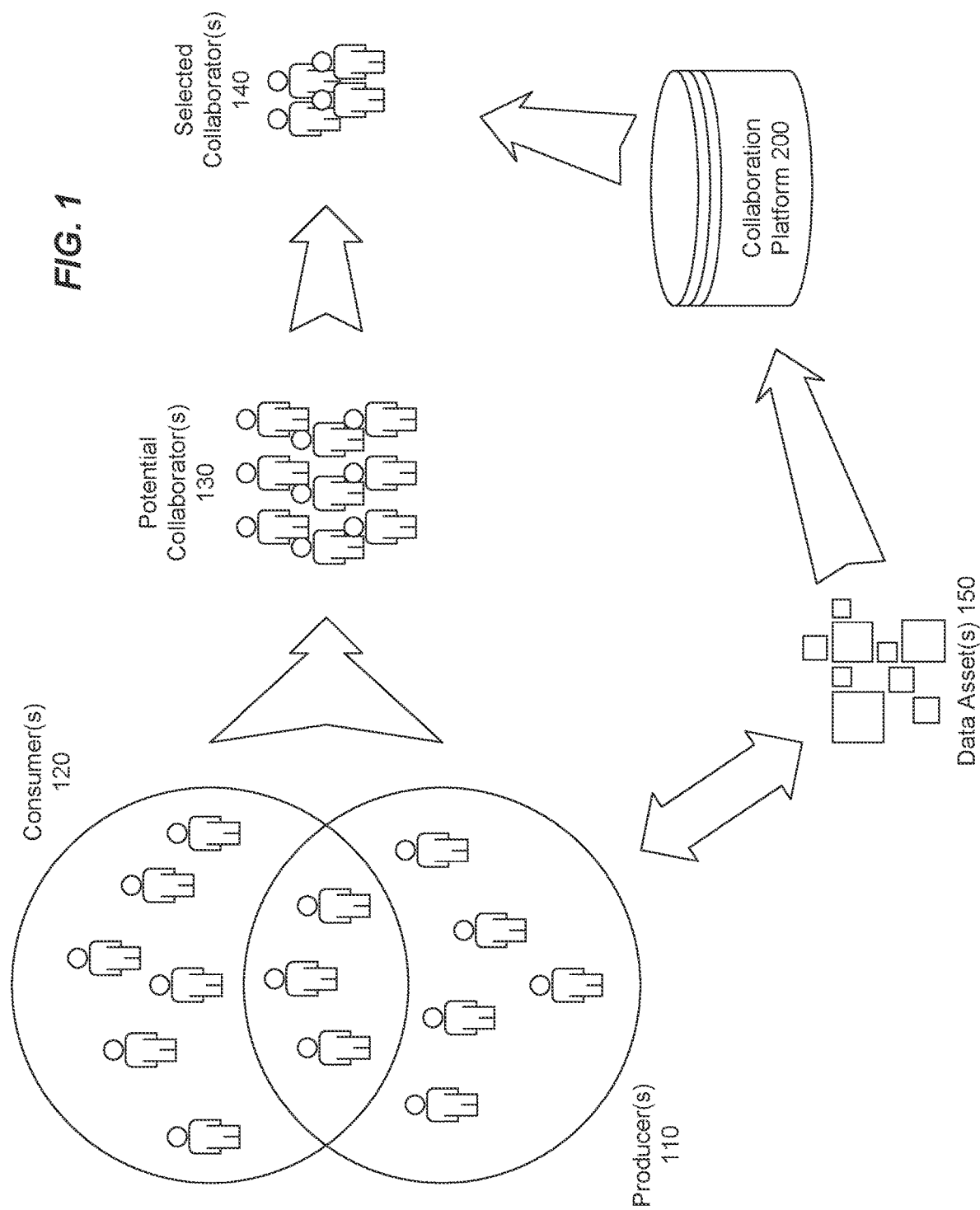
FIG. 1 is a schematic diagram illustrating different types of users and the flow of information, according to an aspect of present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components and steps illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope of the invention is defined by the appended claims.

Embodiments of the present disclosure are directed to a collaboration platform and method of using the platform for performing exploratory or routine analysis for drug discovery and development. The disclosed embodiments may enable creation of insight engines that lead to more drugs, faster and with higher market access potential in areas of highest unmet medical need.

FIG. 1 depicts a schematic diagram illustrating different types of users and the flow of information among them. In some embodiments, the users of the disclosed systems and methods may include scientific groups such as pharmaceutical companies, biotech companies, academic institutions, data aggregators, artificial intelligence (AI) development companies, healthcare payers, nonprofit organizations, government agencies (Census Bureau, CDC, FDA, or other regulatory agencies), or the like. The users may be considered one of two types: producers 110 and consumers 120. As used here, producers 110 may refer to the users that produce data assets 150, and consumers 120 may refer to those that use data assets 150 to carry out R&D projects.

In some embodiments, users may take the role of either producers 110 or consumers 120 based on their goal or perspective. A producer 110 can be a consumer 120 when seeking collaborators for a new project, and a consumer 120 can be a producer 110 by sharing data assets 150 produced through a previous research. For example, an academic institution may be considered a producer 110 where it provides data assets 150 from past projects or a consumer 120 where it wants to start a new project.

Turning to producers 110, users that are considered producers 110 may be those that create data assets 150 and share them to a collaboration platform 200 for collaborations. A data asset 150 is a container comprising one or more related datasets, such as datasets all generated or describing the same research study or clinical trial. A dataset may be a structured file comprising data that relates to a common project, theme, or issue. The data within datasets may be measurements or observations that can be text, numbers, images, or multimedia or algorithms, models, or templates. For example, a dataset may be a collection of variables (e.g., body weight) and their values (e.g., 60 kg) for one or more subjects (e.g., patients). A dataset may include images or videos, such as X-rays, CT (computed tomography) scans, MRI (magnetic resonance imaging) and ultrasound. A dataset may also comprise analytical models such as algorithms or computational models for analyzing datasets. A dataset may also comprise information relating to one or more partners, which are entities that wish to collaborate to solve a specific scientific question or problem. A dataset may also comprise information relating to one or more forums, which are public private collaborations with a common goal, and the information exchanged in such forums. Datasets may be produced from lab exams, medical records, clinical trials, or other similar scientific endeavors. A dataset may comprise some or all of the foregoing types of data. Data assets 150 may comprise some or all of the foregoing types of datasets.

In some embodiments, data assets 150 may follow similar data standard or metadata definitions for quick transfer among systems and/or databases. Such unified scheme of data management may allow for efficient unpacking and understanding of data assets 150 by receiving systems such as those belonging to consumers 120. Such unified scheme may also improve or maximize interoperability among existing tools and applications, which would minimize training and initial cost of setup.

Additionally or alternatively, data assets 150 and subsequent additions or modifications thereto may be managed in a single system. As used herein, the single system may refer to a single unit of hardware (e.g., a single database), a collection of systems or subsystems at a single geographic location (e.g., a server farm), or a single federated database comprising a group of constituent databases interconnected to each other regardless of their geographic locations. Such management scheme may allow data asset 150 to be watermarked and/or tracked (e.g., using blockchain) so that any modifications can be traced to corresponding producers 110 or consumers 120.

Data assets 150 may be made available for free or for a fee payable by consumers 120 if they choose to use data assets 150. While these datasets may have required enormous sums of money to produce, producers 110 may be motivated to share them on collaboration platform 200 for various reasons. For example, pharmaceutical or biotech companies may be motivated to produce these datasets in order to generate insights or find collaborators (e.g., AI development companies) to discover new drugs, which is their core business. Data aggregators may be motivated to produce these datasets to sell them, which is their core business. Academic institutions and patient registries may produce datasets for either or both reasons.

In some embodiments, analytical models may be produced through applying one or more algorithms and/or statistical analyses to datasets to extract useful insights. While the analytical models may also have required enormous sums of money to produce, producers 110 may be motivated to share them on collaboration platform 200 also for various reasons. For example, AI development companies may be motivated to sell their AI models to pharmaceutical or biotech companies. Pharmaceutical or biotech companies may be motivated to produce these models as a consequence of internal exploratory R&D. They may be willing to share these for industry benefit, publications, or improving the analytical models through open-source efforts. Academic institutions may produce analytical models as a part of their research or collaboration with 3rd parties. They may be willing to share these analytical models for publications, improvements through open-source efforts, or sources of funding.

In some embodiments, all analytical models may be built using programming languages compatible with collaboration platform 200 or using specific software development kit (SDK) provided by collaboration platform, which may prohibit harmful applications to function. Analytical models may be tested on datasets and their performances measured for accuracy, efficiency, or both. They may also be reviewed manually by administrators of collaboration platform 200 or by users that have used the analytical models.

Turning to consumers 120, users that are considered consumers 120 may be those that utilize data assets 150. Pharmaceutical or biotech companies and academic institutions may be motivated to consume data assets 150 as a part of their exploratory R&D projects. AI development companies may be motivated to buy the datasets to train their analytical models on better or more data or use the datasets to generate insights to build drugs themselves. Analytical models utilizing AI or machine learning are further improved by additional data for training the analytical models.

Consistent with the disclosed embodiments, collaboration platform 200 may search through available producers 110 and consumers 120 to match potential collaborators 130 to a user project. Potential collaborators 130 may include a collection of producers 110 and consumers 120. The process with which potential collaborators 130 are identified is described below in more detail.

Potential collaborators 130 may also go through a selection process to arrive at selected collaborators 140. Selected collaborators 140 may include a combination of producers 110 that are selected by the owner user that initiated the corresponding user project (e.g., consumer 120). Selected collaborators 140 and the owner user may be granted access to data assets 150 produced by selected collaborators 140 once they agree to collaborate with the owner user and the collaboration is enabled by collaboration platform 200. The process with which selected collaborators 140 are determined is described below in more detail.

Figure 2:
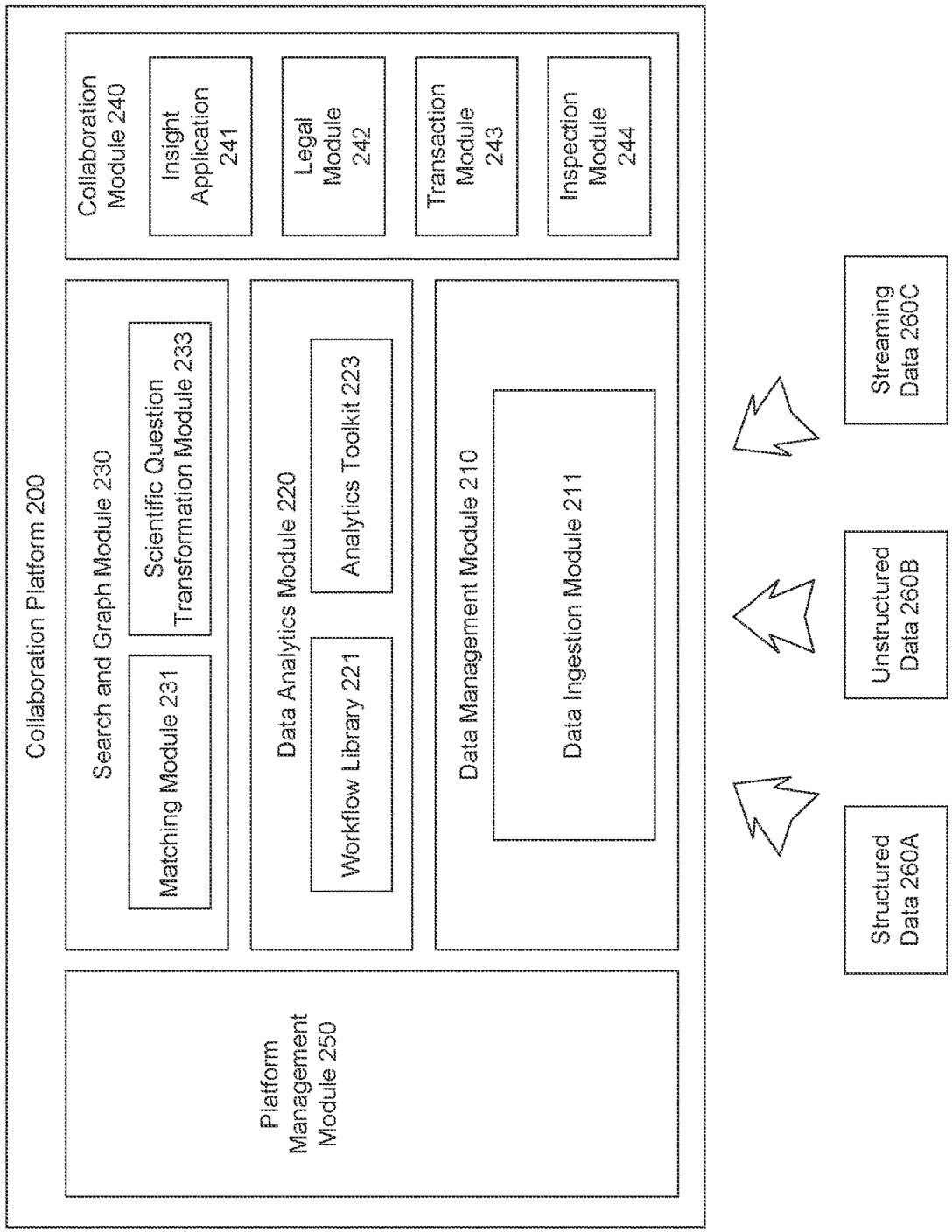
FIG. 2 is a schematic block diagram illustrating an exemplary embodiment of a collaboration platform, according to an aspect of present disclosure.

FIG. 2 depicts a schematic block diagram illustrating an exemplary embodiment of a collaboration platform 200. Consistent with disclosed embodiments, collaboration platform 200 may allow different producers 110 to allow their data assets 150 to be used by a shared environment while retaining access control to protect their intellectual property. Additionally, collaboration platform 200 may allow for producers 110 to access and create projects utilizing their own data assets 150, without collaborating with additional producers 110, consumers 120, or collaborators 140. Collaboration platform 200 may be designed such that outcomes (e.g., datasets, new use cases, or new treatments) of user projects can be shared or published but not the elements that contributed to it (e.g., utilized data assets 150, methods of analyses).

Collaboration platform 200 may comprise at least one processor and at least one non-transitory computer-readable medium containing instructions. When executed by the at least one processor, the instructions can cause the system to perform operations such as those performed by the modules depicted in FIG. 2. Platform 200 may include a variety of modules, each of which may be implemented as a functional unit within a processor, discrete system, or any combination thereof. The modules may be connected to one another via one or more public or private network connections including the Internet, an intranet, a WAN (Wide-Area Network), a MAN (Metropolitan-Area Network), a wireless network compliant with the IEEE 802.11a/b/g/n Standards, a wired network, or the like. In further embodiments, collaboration platform 200 or any of its component modules, individually or in any combination, may take the form of a server, general-purpose computer, a mainframe computer, a special-purpose computing device such as a graphical processing unit (GPU), laptop, or any combination of these computing devices. Collaboration platform 200 may also be a stand-alone system, or it may be part of a subsystem, which may be part of a larger system.

While the depicted modules include a data management module 210, a data ingestion module 211, a data analytics module 220, a workflow library 221, an analytics toolkit 223, a search and graph module 230, a matching module 231, a scientific question transformation module 233, a collaboration module 240, an insight application 241, legal module 242, transaction module 243, inspection module 244, and a platform management module 250. Other modules and components not depicted may also be included in collaboration platform 200. For example, one or more networked databases (not depicted) may also be a part of collaboration platform 200, where they are configured to store data assets 150 shared by producers 110.

Turning to individual modules, data management module 210 may be configured to process and connect data assets 150 among different entities. Raw data (e.g., structured data 260A, unstructured data 260B, streaming data 260C described below) that are introduced to collaboration platform 200 may pass through data management module 210 to be packaged into data assets 150. In some embodiments, data management module 210 may comprise pipelines, schema, and ontologies that help process, structure and connect data assets 150.

A pipeline is one or more software processes executed in an order such that the output of one process is the input to the next. A pipeline may be designed in a modular fashion comprising one or more of parsers, templates, shared libraries, and/or business rules. Modular design of pipelines may allow individual components (e.g., parsers, templates, shared libraries, or business rules) to be repaired or replaced independently of the others. Series of repairs or replacements of the individual components may lead to a more mature pipeline that are better configured to process data in different formats or modalities.

Within a pipeline, a parser is a software component that takes input data in its native format and converts the data into one or more formats compatible for use with collaboration platform 200. Pipelines may be used to convert any data format associated with a data asset 150 to platform-preferred schema.

In some embodiments, pipelines may comprise templates that help facilitate the process of curation by standardizing certain steps. For example, a template may be configured to apply a certain set of functions or transformation to a common type of data. In further embodiments, pipelines may comprise shared libraries where a more complex set of transformations are necessary to process a particular type of data. Shared libraries may comprise a set of transforms stored as executable libraries that may be called upon as needed in the process of integrating raw data. Additionally or alternatively, pipelines may comprise business rules, which are a set of custom logic or algorithm that are not standardizable or specific to the data owner's (e.g., producer's requests).

A schema is a diagram or model that represents the structure of data in a dataset. Schema may be created by learning from harmonizing multiple data sets from various sources. For example, a target clinical data schema may be designed by reviewing schema of multiple prior trials and harmonizing the data across trials. For example, a schema may be created by including common structures or variables of multiple schema from prior trials such as physiological parameters (e.g., sex) or trial parameters (e.g., trial duration). This schema may then be expanded to include additional parameters necessary for a new trial (e.g., new physiological measurements under study).

In another example, a schema may be designed where harmonization of schema from multiple different trials on Alzheimer lead to a finding that LDL cholesterol levels of patients are often measured. A new schema designed from such finding may include LDL cholesterol level as a potential biomarker for Alzheimer in addition to the usual biomarker—amyloid plaques. Harmonization and design of schema may be automated using artificial intelligence or machine learning to recognize such repetitive occurrence of previously unnoticed phenomenon, thus potentially leading to new discovery.

An ontology is a set of concepts and categories in a subject area or domain that shows the properties and the relations between the data. An ontology may be provided or may be developed by harmonizing data, linking similar and different data types and creating terms and their attributes in a structured fashion.

Data management module 210 may be configured to receive data assets 150 from producers 110 and integrate them into the different workflows and analyses supported by the other modules of collaboration platform 200.

In some embodiments, data assets 150 can include analytical models and datasets as discussed above, where the datasets can include structured data 260A, unstructured data 260B, or streaming data 260C. Datasets of some embodiments may also include images. Each data asset 150 received by data management module 210 may be accompanied by a schema describing how data asset 150 is organized or what the previous user project that produced data asset 150 was characterized. Data management module 210 may use these schemas, as discussed below, to index and search through different data assets 150 stored in collaboration platform 200. Platform 200 may update or modify schema as increasing numbers of data assets 150 are integrated into platform 200, and categories, groups, or modalities may be able to link data assets 150 across diseases or other common characteristics. Schema may be specific to data type, groups, attributes, categories, modalities, or any other individual or communal characteristic associated with a data asset. For example, schema may be associated with data type such as genomics, proteomics, trial type, disease area, medical images, or any variable originated during a collaboration.

Furthermore, data management module 210 may, in some embodiments, receive data assets 150 in stages. For example, producer 110 may share only a portion of its data assets 150 such as a representative sample or their schema for public access. Producer 110 may then share the full version of its data assets 150 after selected collaborators 140 accept the project and begin working together. To this end, data management module 210 may control access to various portions of data assets 150 by limiting what information is shared with potential collaborators and preventing any sensitive data from being shared forward. This may ensure that the intellectual properties and data assets 150 that users bring to collaboration platform 200 are protected and secured.

In some embodiments, data management module 210 may comprise a data ingestion module 211 configured to specialize in integrating datasets among data asset 150. Data ingestion module 211 may condition datasets received from producers 110 to adopt common standards and associated ontology. As data is ingested, the profile of the data is known or can be identified. For example, the data may be a specific data type (such as clinical or genomics) or a specific disease area (such as Alzheimer's or heart disease). Variables may be mapped to equivalent fields in the schema and/or ontology being used by the platform for these specific data types or diseases. If incoming datasets have attributes that are not in the common schema or ontology, the data field may be added to the schema or ontology. Alternatively, these unrecognized attributes may be not mapped. The ingested data may be stored in a database and made available to consumers 120 and selected collaborators 140 for concurrent access.

In some embodiments, one or more ontologies may be developed by linking similar and different data types and creating terms and their attributes in a structured fashion. A machine learning algorithm may scan through linkages made by human operators in the past and suggest specific ontologies that link multiple data types. Additionally or alternatively, the machine learning algorithm may learn such linkages through feedback provided by users on resulting ontologies. Platform 200 may update or modify the one or more ontologies as increasing numbers of data assets 150 are integrated into platform 200. This allows for refinement and improvement of the ontology by the incorporation of previously unknown attributes and any insights generated on the platform 200.

In some embodiments, data ingestion module 211 may be configured to parse the received datasets to identify data elements with known tags or indices. And once parsed, data ingestion module 211 may normalize groups of data elements (e.g., a column of data elements) to a standard unit in accordance with usual practices (e.g., metric units) and update associated data elements to reflect the normalization. For example, data ingestion module 211 may recognize that a group of data elements represent body weight and convert their units to kilograms. Data ingestion module 211 may also update associated data elements for dosage to be based on kilograms instead of pounds.

Another feature of data ingestion module 211 may include harmonizing data elements so that they follow a common convention. For example, one dataset may indicate gender with values "male" and "female," while another dataset may indicate the same with values "M" and "F." In these cases, data ingestion module 211 may replace each indication to use "male" and "female." Any other set of indications may be used as long as they are kept consistent across different datasets. In some embodiments, harmonizing data elements may also include making each data element consistent by transforming the data elements to standard data types based on the ontology. For example, a column of data elements corresponding to the same variable may include data types: integers, doubles, or texts due to a parsing error. In these cases, data ingestion module 211 may convert the data elements to be a same data type. Such inconsistencies may be recognized by human operators, producers 150, or a machine learning algorithm, which, upon discovery of a new inconsistency, may be equipped to create new custom rules that can automatically convert the inconsistent data element.

In further embodiments, data ingestion module 211 may be configured to perform "health checks" on a received dataset, where the module identifies known data elements and checks to see if the values for this data element are within usual or known safety ranges. For example, data ingestion module 211 may be able to identify that a group of data elements represent body weight and recognize that body weights are usually less than 200 kg. In this case, a data element, for example, with a value of 300 in a column for body weights in kilograms may suggest that the data point is supposed to be in pounds despite the specified unit. Data ingestion module 211 may then convert the data element with a value of 300 to be 136, the kilogram equivalent of 300 lbs. The conversion may occur automatically or with user input or confirmation. In some embodiments, data ingestion module 211 may be configured to identify the data elements based on columns pre-defined in the corresponding schema; or associated tags or indices. In some aspects, health checks may be assigned at the level of a variable, such as body weights discussed above, but may also be at an aggregate level (e.g., patient). Health checks may also involve checking to see that a patient record comprises data in all the expected fields for the type of patient. For example, if the record is one of a patient being treated for cardiovascular issues, the list of medications for this patient would be expected to include a statin. The list of expected data could be developed by medical professionals or researchers or generated from data on the platform. The list of expected data could also be continually updated using machine learning.

Still further, data ingestion module 211 may be configured to populate received datasets into a set of knowledge base templates with predetermined columns and parameters that are associated with the same ontology. This may occur when the received data is missing tags or labels that allow data ingestion module 211 to recognize and ingest the received data. In some embodiments, data ingestion module 211 may populate the received dataset based on manual determination and inputs from one or more administrators of collaboration platform 200 or based on automatic determinations of machine learning algorithms.

In some embodiments, data management module 210 may also comprise one or more additional modules (not depicted) configured to anonymize data assets 150. Anonymizing data assets 150 may comprise recognizing and removing personally identifiable information from data assets 150. Such information may include, for example, a full name, Social Security number, driver's license number, bank account number, passport number, email address, or any other information that can allow a third party to identify a particular person. In some embodiments, anonymizing data assets 150 may comprise anonymizing medical images by defacing to remove, for example, some or all of a face making it impossible to recognize the subject. In some embodiments, data management module 210 or the responsible module may anonymize the received dataset by assigning a unique global identifier to each group of data elements (e.g., group of data elements corresponding to a patient) and reorganizing the other data assets 150 with the same unique global identifiers where they had been associated with the same patient.

Referring back to individual modules of collaboration platform 200, data analytics module 220 may be configured to provide a workflow library 221 and an analytics toolkit 223. Workflow library 221 and analytics toolkit 223 may be made available to selected collaborators 140 for use to explore their own data assets 150 or as they form a collaboration and begin a user project.

In some embodiments, workflow library 221 may store or include prebuilt analytic templates that capture routine and innovative analyses that consumers 120 frequently perform. Some analytic templates may also be based on machine learning algorithms. In some embodiments, prebuilt analytic templates may be used at least in part to identify analytic methods best suited for the scientific questions proposed by consumers or collaborators. The prebuilt analytic templates may include analysis tools such as those used for statistical analysis, genome-wide association study (GWAS), Chi-squared test, regression analysis functions, or the like. The analysis tools may also be grouped for specific disease areas such as immunology, neurodegenerative diseases, or cardio-metabolic diseases. Furthermore, the analysis tools, within each disease area, may also be organized by stages such as discovery (e.g., virtual proof of concept indicator (vPOC) or graph mining), pre-clinical (e.g., adverse event predictor or cellular image analysis), clinical trial (e.g., endpoint explorer or virtual trial design), or market access (disease progression map).

In certain embodiments, analytics toolkit 223 enables platform users to further analyze the data. For example, analytics toolkit 223 may include an integrated development environment for statistical computing and graphics, applications of high-level and general purpose programing language, open-source software libraries, symbolic math libraries based on dataflow and differentiable programming, and other software or application based elements to enable a user to further explore data assets 150. Analytics toolkit 223 may also comprise machine learning algorithms and/or software components.

Collaboration platform 200 may also comprise search and graph module 230 for generating a user project for collaboration and determining matching data assets 150 and potential collaborators 130. In some embodiments, search and graph module 230 may receive a search query from consumer 120, where the search query may comprise different parameters or a scientific question that consumer 120 wishes to explore. These parameters and scientific question may be converted to user projects and matched to data assets 150 based on the algorithms described below.

In some embodiments, a user project may comprise a wide variety of attributes (e.g., description, disease classification, use case classification, linked projects, linked drugs, linked clinical trials), datasets, and code for analysis or transformation. Attributes may include lines of code or may be populated through a code. For example, a particular attribute that is determined as a function of other attributes in a project may be expressed in code, such that the attribute may be automatically populated upon application to data asset 150.

Figure 3:
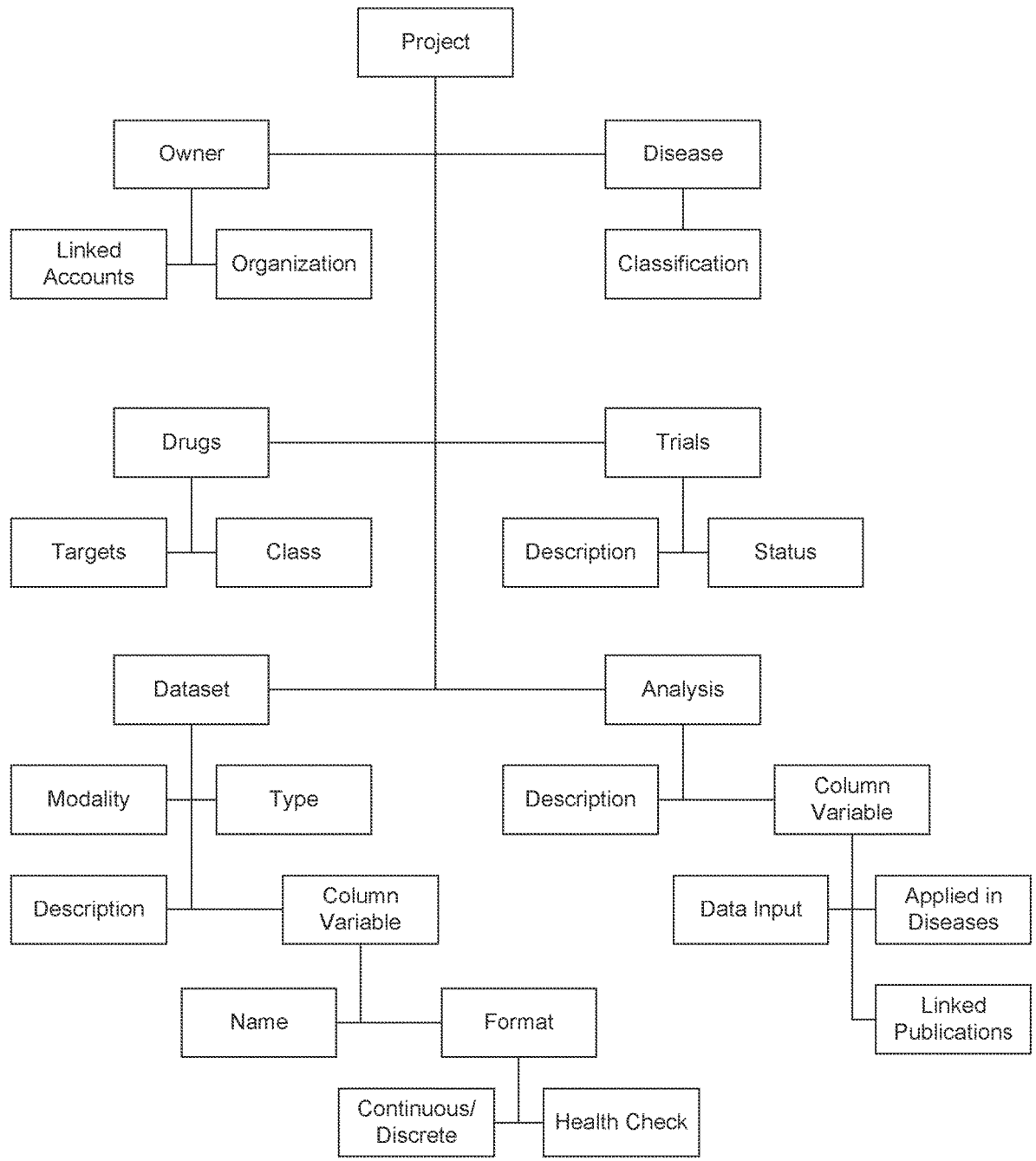
FIG. 3 is an exemplary project template depicted as a tree structure showing a subset of attributes a user project may include, according to an aspect of present disclosure.

FIG. 3 shows an exemplary project template depicted as a tree structure showing a subset of attributes a user project may include and how they are organized. A project may have only some of the fields populated. A project for a dataset, for example, may have only those fields shown under "dataset" populated. A project for an AI model may have only those fields shown under "analysis" populated. Furthermore, attributes may be populated based on the keywords, filters, natural language, dropdown menus that consumer 120 selects, or by other methods. Additionally, attributes may be populated as the result of a machine learning algorithm parsing the scientific question consumer 120 submitted.

Search and graph module 230 may use a similar process to index data assets 150 from producers 110, where certain data assets 150 may be stored with corresponding producer projects that were used to start the collaboration that produced data assets 150. In some aspects, metadata, schema, or portions of the data assets 150 may be stored with corresponding producer projects. In this way, search queries from consumers 120 may be converted to user projects and previous collaborations and data assets 150 may be associated with producer projects, where search and graph module 230 may match consumers 120 to producers 110 by matching the user project to producer projects. The owners of matched data assets 150 may then be presented to consumer 120 as potential collaborators 130. In some embodiments, search and graph module 230 may also translate and index schema of data assets 150 into platform-required schema. In some embodiments, where schema associated with a data asset may include an unknown or new variable not yet identified by platform 200, the schema may need to be translated into platform-required schema by a platform administrator.

The actual matching of consumers 120 to potential collaborators 130 may be done using a matching module 231 and scientific question transformation module 233 of search and graph module 230. The two matching modules may be configured to match a user project to producer projects and present potential collaborators 130 corresponding to the matched data assets 150. In some embodiments, consumer 120 may also search for a specific provider 110 or a consumer 120 by name or organization affiliation.

Matching module 231 may be used to match the user projects where certain parameters are used. In a first instance, consumer 120 may initiate the matching process by submitting keywords, filters, or dropdown menus. While different parameters may be submitted based on consumer 120's preference, parameters for analytical models among data assets 150 may include types of producers 110 (e.g., academic institution or a pharmaceutical company), disease area, problem statement, performance requirements, privacy, or the like. Parameters for datasets may include disease area, type of the dataset, time scale of the dataset, population specification, producer name, privacy or the like.

In another instance, consumer 120 may select one of the recommended combinations of data assets 150 or producers 110 that are customized based on consumer's 120 profile. For example, matching module 231 may analyze consumer's 120 past activities (e.g., frequently explored disease areas, previous projects, shared data assets 150, or forum posts). Matching module 231 may also analyze other users' activities to recommend popular data assets 150 that are frequently used by other users.

In yet another instance, consumer 120 may select other users or data assets 150 from a matching panel, where different producers 110, data assets 150, or other consumers 120 soliciting new collaborators may be listed.

Matching module 231 may be adaptive in nature. That is, as collaborations are performed, ontology and schema associated with various data assets may update or change. Additionally, new data assets may be created as a result of collaborations. As such, as links between the various data assets are created, the matching module may identify the most promising data assets for use in a collaboration associated with a specific scientific question. Matching module 231 may use two different algorithms: qualitative matching and quantitative matching. Other algorithms for identifying similar objects are also within the scope of this disclosure but not enumerated herein.

In some embodiments, qualitative matching may utilize keyword matching in schema or metadata associated with data assets or rely on ontology mapping. Qualitative matching may use disease tags, such as those registered in Medical Dictionary for Regulatory Activities (MedDRA) or data types (e.g., genomic, interventional trial, electronic health records, etc.). For example, given a particular data asset 150 that has been used in multiple projects in the past, an analysis of the past projects may reveal frequent mentions of a disease (e.g., multiple sclerosis). The particular data asset 150 may thus be tagged as being relevant for multiple sclerosis and show up when a user searches for multiple sclerosis. In further embodiments where there are multiple such data assets 150 for a particular keyword, matched data assets 150 may be ranked based on the volume of data asset (e.g., number of patients) or the number of unique samples. Additionally or alternatively, specifications by consumer 120 may be set as additional attributes of a user project, which are matched to data assets 150 using one or more qualitative filters.

On the other hand, quantitative parameter matching may be based on the schema of the user project and data assets 150. For example, column titles and frequency may be used to establish relevance, where search and graph module 230 may search through column titles of data assets 150 for qualitative criteria. Quantitative matching may identify data assets that include one or more desired variables and identify an amount of data associated with the one or more desired variables. A data asset having more data associated with the one or more desired variable may be ranked higher than a data asset having the one or more desired variable but with less data. Search and graph module 230 may perform health checks on the matched columns before indicating that the corresponding data asset 150 is a match.

In certain embodiments, a scientific question may be entered by a user in natural language, transformed into a project by, for example, question transformation module 233, and used to identify potential collaborators. Scientific question transformation module 233 may be configured to parse the scientific question using natural language processing and identify attributes to populate a user project based on the ontology.

An exemplary method of transforming a scientific question into a user project is shown below with respect to FIG. 6. As a simple example, a user may enter a scientific question using a user interface (UI). In this example, the scientific question may be a hypothesis: "Elevated LDL is linked with Alzheimer's progress." Scientific question transformation module 233 may parse the scientific question using natural language processing techniques and identify attributes for a user project based on the ontology. For example, the transformation module 233 may recognize that the question relates to Alzheimer's and may determine that the question type is "disease progression" based on the use of the word "progression." Transformation module 233 may determine that the question is in the disease area "neuroscience" based on the word "Alzheimer's." Based on this information, the transformation module 233 may infer data used to populated other fields of the user project. For example, because the exemplary question relates to Alzheimer's and disease progression, the transformation module 233 may choose methods, such as latent class mixed modeling or K-means clustering.

In some aspects, scientific question transformation module 233 may convert a natural language scientific question presented by a user or consumer 120 into a code that is an analytical representation of the scientific question. The code may be derived from platform data ontology and schema, previous scientific questions, prebuilt analytic templates stored in the workflow library, and insights generated on the platform during previous collaborations. All data assets integrated on platform 200 may be converted to a similar code representing one or more collaborations, projects, or linking the data assets to one or more scientific questions through schema or ontology.

Scientific question transformation module 233 may then provide the resulting user project to matching module 231 for use in identifying matching data assets 150, potential collaborators, AI models, and partnerships on a qualitative basis discussed above. Based on similarity of the scientific question presented by the user or consumer 120 and scientific questions linked or associated with data assets, matching module 231 may determine a match. Each match may include a similarity value, which represents a percentage of similarity between the scientific question presented by the user or consumer 120 and one or more data assets, to allow for rankings of matched data assets.

Once search and graph module 230 has finished matching the user project to producer projects and thus the data assets 150, potential collaborators 130 corresponding to the matched data assets 150 are presented to consumer 120 for selection. Search and graph module 230 may present the recommended matched data assets 150 to the consumer 120 based on the rankings. Consumer 120 may then select a subset of potential collaborators 130, which search and graph module 230 will then relay to collaboration module 240.

In some embodiments, search and graph module 230 may present potential collaborators 130 by ranking them based on how closely the producer projects match the user project. For example, search and graph module 230 may determine the ranks based on the number of matching attributes; most popular data assets selected in the past by previous users; or the type of scientific question. The rank information may be presented only to consumer 120, and individual potential collaborators 130 may not be aware of their ranking in the particular search initiated by consumer 120.

In further embodiments, search and graph module 230 may display short descriptions of data assets 150 along with each potential collaborator 130. The short descriptions may be provided by the corresponding provider 110 with data asset 150 or generated by data management module 210 based on its schema. Additionally or alternatively, consumer 120 may also be given limited access to the matched data assets 150 using the inspection module 244. Inspection module 244 may allow for access to a portion of the matched data asset 150 for preview before purchasing or building a collaboration using the matched data asset 150. In some embodiments, the portion of the matched data asset 150 may be publicly available or have been authorized for release by the corresponding producer 110. Inspection module 244 may perform or may be used to perform one or more data quality checks on a matched data asset 150. In a data quality check, a user may be allowed to run queries on the matched datasets to see if any of the matched datasets is suitable for the user's use. For example, a user that is researching a question relating to heart disease may run a query on a dataset to determine if parameters relating to heart disease are appropriately populated. In certain embodiments, inspection module 244 may be integrated with data ingestion module 211 to display results of previously performed data quality checks associated with ingested data assets.

In some embodiments, search and graph module 230 may further comprise a recommendation module (not depicted) configured to output an optimized combination of data assets 150 and corresponding potential collaborators 130 that return the highest match. Such optimized combination may be displayed to consumer 120 in a distinguished manner (e.g., highlighted to assist in selecting the collaborators). The recommendation module may use the ratings and comments provided by users of the system to improve or rank data assets 150, methods, models, partnerships, or other inputs to the platform.

Collaboration platform 200 may also comprise collaboration module 240 for securely and seamlessly coordinating a collaboration between consumer 120 and selected collaborators 140 selected from the pool of potential collaborators 130. Once consumer 120 has chosen selected collaborators 140, collaboration platform 200 may generate and transmit a notification to each selected collaborator 140. The notification may include the identity of consumer 120, a description or abstract of the user project, identities of the other selected collaborators 140, or any other information that may be useful for respective selected collaborator 140 to decide whether to collaborate with consumer 120 or not. The description or abstract of the user project may be redacted or provided by consumer 120 to ensure sensitive information is not yet shared, because selected collaborators may choose to reject the collaboration.

When each selected collaborator 140 accepts the collaboration, collaboration module 240 may be configured to finalize the collaboration by recording contracts and payments. In some embodiments, a legal module 242 may allow a selected collaborator 140 to generate one or more contracts (e.g., memorandum of understanding, joint research agreement, non-disclosure agreement, etc.) between consumer 120 and each selected collaborator 140. One or more contracts may be generic or configurable for a specific situation, by, for example, dropdown menus or prompts guiding each selected collaborator 140. Legal module 242 may then obtain indications of acceptance or rejection from each of consumer 120 and selected collaborators 140, which may comprise signed copies of the contracts. In some embodiments, the contract may include a fee arrangement for using a data asset 150, which would require a payment between the affected parties. In this case, collaboration module 240 may include a transaction module 243 configured to receive payment information from the payer and exchange the electronic payment according to the contracts. Transaction module 243 may be configured to receive various types of payment, such as credit card, bank transfers, PayPal, or other payment types. Transaction module 234 may also be configured to manage payment to one or more collaborators 140 or one or more consumers 120 depending on any arrangements defined by the legal module 242. Transaction module 243 may also provide a legal disclaimer regarding the payment or the use of data asset 150.

Once every party has accepted the collaboration, executed the contracts, and exchanged payments, collaboration module 240 may authorize a full disclosure of any data assets 150 belonging to selected collaborators 140 that had been restricted. Providers 110 among selected collaborators 140 may also share a full set of data assets 150, where only a portion of data assets 150 was previously imported into collaboration platform 200. The new full set of data assets 150 from such providers 110 may be temporarily imported into collaboration platform 200 through data management module 210 until the conclusion of the collaboration.

In some embodiments, collaboration module 240 may be configured to allow consumer 120 and selected collaborators 140 to set up and manage various trials (e.g., animal trial, virtual trial, or clinical trial). For example, collaboration module 240 may assist in recruiting patients, anonymizing their data, and making them available to consumer 120 and selected collaborators 140 for analysis. In further embodiments, collaboration module 240 may also be configured to allow consumer 120 and selected collaborators 140 to manage grant applications to private and public sources (e.g., National Institute of Health, Gates Foundation, or other organizations that award grants or loans).

Collaboration module 240 may also comprise an insight application 241 configured to generate and/or store insights determined based on operation of collaboration platform 200.

Scientific insights are generated as a part of use cases being solved. Scientific insights may be stored as a knowledge graph on the platform. For example, the identification of relationship between LDL cholesterol level and Alzheimer discussed above may be a scientific insight generated through the use of collaboration platform 200. Insights may be validated by human experts or intermediaries who qualify that particular insights are valid and derived from trusted sources by trusted and rightful contributors. Consumer insights may be, for example, rating and/or comments that assist with ranking data assets, AI models, potential collaborators and other items on the platform. Consumer insights and/or rankings may be used to help solve scientific questions.

The owner/creator of an insight may be determined based on consideration of contribution. Such determination may then dictate accessibility to the insight. For example, a scientific insight may be assigned or attributed to contributors of the project that generated the insight (e.g., producers 110 or selected collaborators 140). The insight may then be accessible to only the contributors of the project as a private insight. In another example, an insight may be generated by connecting public clinical trial data (e.g., from clinicaltrials.gov) to specific publications in academic journals and/or patents. A natural language processing algorithm may be used to extract hypotheses from publications or patents so that the public data can be used to validate the hypotheses and form an insight. Such insight may be made available to all users of collaboration platform 200. Still further, a consumer insight may be generated by identifying relationship among individual users of collaboration platform 200 (e.g., who they are connected to, which organization they are affiliated with, which data assets 150 they have used, which projects they are a part of, etc.) Such insight may be used as a global browser of ongoing projects and their progress to date or as networking means to form new connections or collaborations. These insights may be partially restricted for viewing as they may include sensitive/private information.

In some embodiments, the owner/creator of an insight in a knowledge graph may decide to connect their personal knowledge graph with platform's common knowledge graph (making it searchable but not accessible). Shared knowledge graphs can help improve ontology and help automatically include necessary fields when creating a collaboration search request.

Insight application 241 may be configured to generate disease specific inferences related to the scientific question using data assets 150 received and ingested for the collaboration; receive feedbacks from consumer 120 and selected collaborators 140 on the appropriateness of the matching, on how each collaborator has been, or on how the platform has been. In some embodiments, the feedbacks may also include comments on the quality of data assets 150 provided by selected collaborators 140. Insight application 241 may then use the inferences and feedbacks to improve the search and graph module 230 (e.g., adjust ranking or indexing).

Furthermore, collaboration platform 200 may comprise platform management module 250, which may comprise administrative and miscellaneous modules (not depicted) for managing the platform (e.g., logging, authentication, API management, billing/usage reporting, service monitoring). Platform management module 250 may also comprise input/output devices or terminals configured to allow administrators of collaboration platform 200 access individual modules or components. In some embodiments, platform management module 250 may also be configured to provide a forum where providers 110 and consumers 120 can freely share ideas, post questions, or publish data assets 150. Such forum may promote interactions and new collaborations to form among providers 110 and consumers 120.

In some embodiments, collaboration platform 200 may comprise user interface 252 by which users of the collaboration platform 200 may enter data, scientific questions, responses, or selections. Collaboration platform may also comprise one or more display devices on which users view data, choices, and other information. In some embodiments, one or both of user interface 252 and the display devices may be part of or share functionality with platform management module 250. In some embodiments, they are independent modules.

Figure 2A:
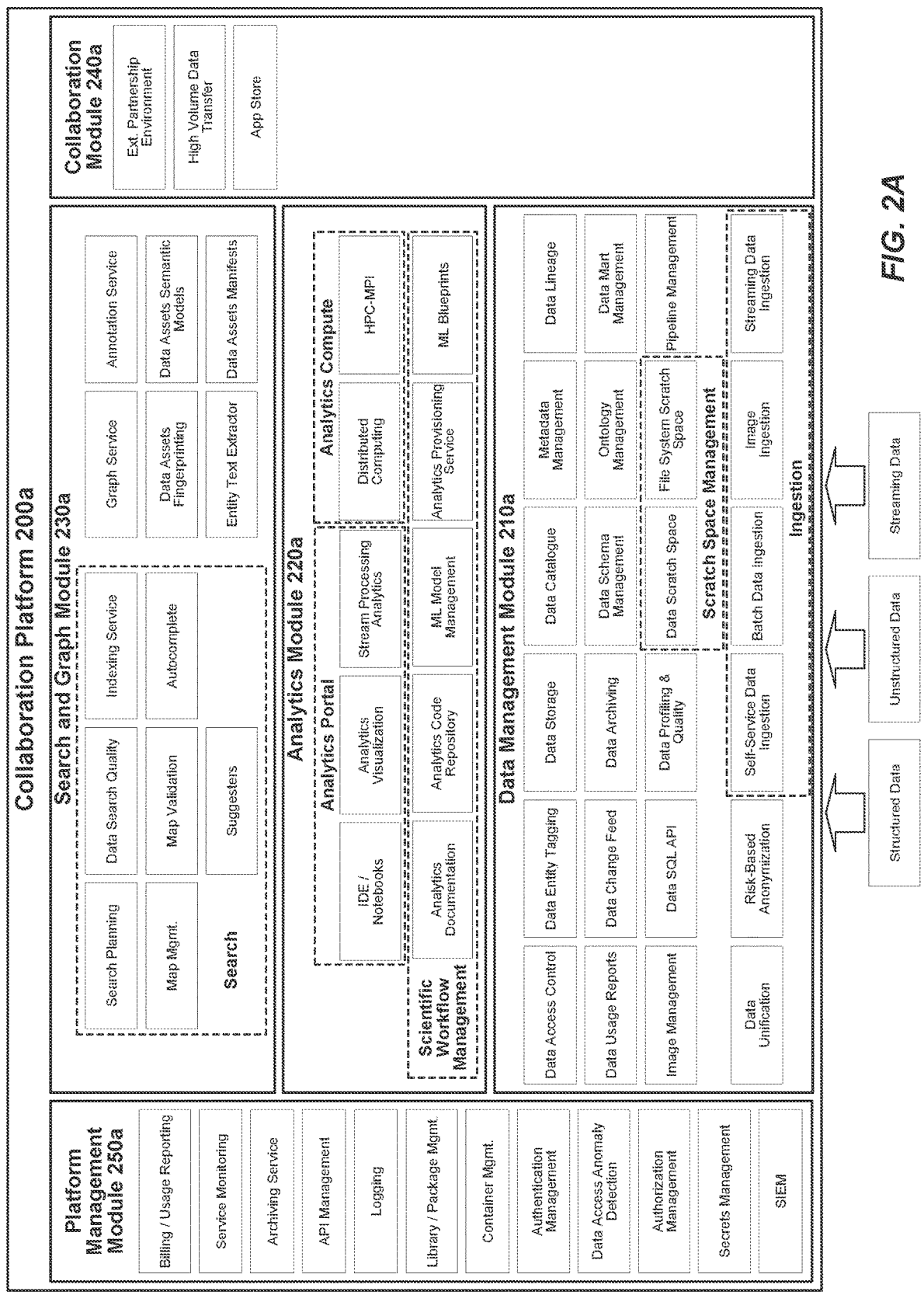
FIG. 2A is a schematic block diagram illustrating an alternate exemplary embodiment of a collaboration platform, according to an aspect of present disclosure.

FIG. 2A depicts a schematic block diagram illustrating an alternate embodiment of a collaboration platform 200a having additional components, not all of which are described herein. Consistent with disclosed embodiments, collaboration platform 200a may allow different producers 110 to allow their data assets 150 to be used by a shared environment while retaining access control to protect their intellectual property. Additionally, collaboration platform 200a may allow for producers 110 to access and create projects utilizing their own data assets 150, without collaborating with additional producers 110, consumers 120, or collaborators 140. Collaboration platform 200a may be designed such that outcomes (e.g., datasets, new use cases, or new treatments) of user projects can be shared or published but not the elements that contributed to it (e.g., utilized data assets 150, methods of analyses). Collaboration platform 200a may include a data management module 210a, an analytics module 220a, a search and graph module 230a, a collaboration module 240a, and a platform management module 150a.

Figure 4:
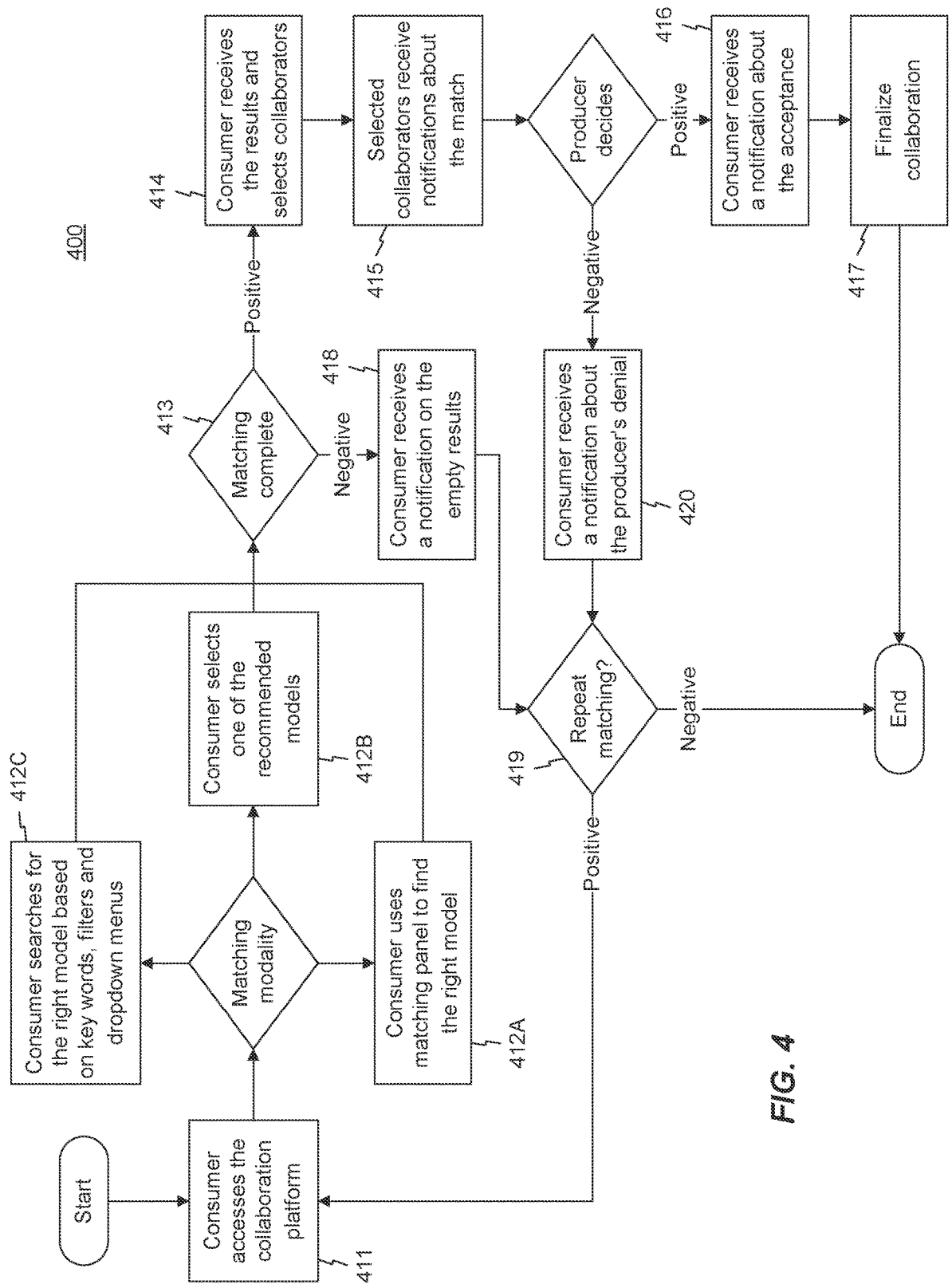
FIG. 4 is an exemplary flowchart of a computerized process for matching a user project with collaborators using consumer specified data, according to an aspect of present disclosure.

FIG. 4 is an exemplary flowchart of a computerized process 400 for matching a user project with potential collaborators 130 using parameters specified by consumer 120. Process 400 may be performed by collaboration platform 200 using different components thereof discussed above.

Process 400 may begin at step 401 with consumer 120 accessing collaboration platform 200. Matching module 231 may then receive the parameters from consumer 120 via search and graph module 230 in any of the three instances discussed above, as represented by steps 412A-412C. For each of steps 412A-412C, matching module 231 may attempt to match the received parameters to data assets 150 in the processes discussed above. For example, matching module 231 may convert the parameters into attributes of a user project; identify potential data assets 150 by comparing the attributes of the user project to attributes of the producer projects associated with data assets 150; and present potential collaborators 130 corresponding to the potential data assets 150.

At step 413, the matching is complete, and at step 414, consumer 120 may choose selected collaborators 140. Having received consumer's 120 selections, collaboration module 240 may notify selected collaborators 140 about the match and the user project in the manner discussed above at step 415. Next, an acceptance by selected collaborator 140 may prompt collaboration module 240 to notify consumer 120 about the acceptance, at step 416, and proceed to finalizing the collaboration, at step 417, as discussed above.

On the other hand, however, the matching process in process 400 can go awry in a number of different ways. For example, matching module 231 may be unable to match the user project to any data asset 150, at step 418, at which point search and graph module 230 may notify consumer 120 on the empty results. In some embodiments, search and graph module 230 may also prompt consumer 120, at step 419 on whether he or she wishes to reattempt matching with a different set of parameters. A positive response by consumer 120 may prompt search and graph module 230 to go back to step 411 and restart process 400.

In another example, the matching process may go awry when selected collaborator 130 declines consumer's 120 request for collaboration. In such cases, collaboration module 240 may notify consumer 120 of the denial, at step 420, and prompt him or her on whether he or she wishes to reattempt matching, at step 419. A positive response by consumer 120 may also prompt search and graph module 230 to go back to step 411 and restart process 400.

In further embodiments, consumer 120 or producer 110, depending on who initiated the matching, may be given an option to reject all potential collaborators 130 matched at step 413. If so, search and graph module 230 may prompt whether the matching should be repeated at step 419. Selection of one or more potential collaborators 130 at step 414 would allow process 400 to proceed as discussed above.

Figure 5:
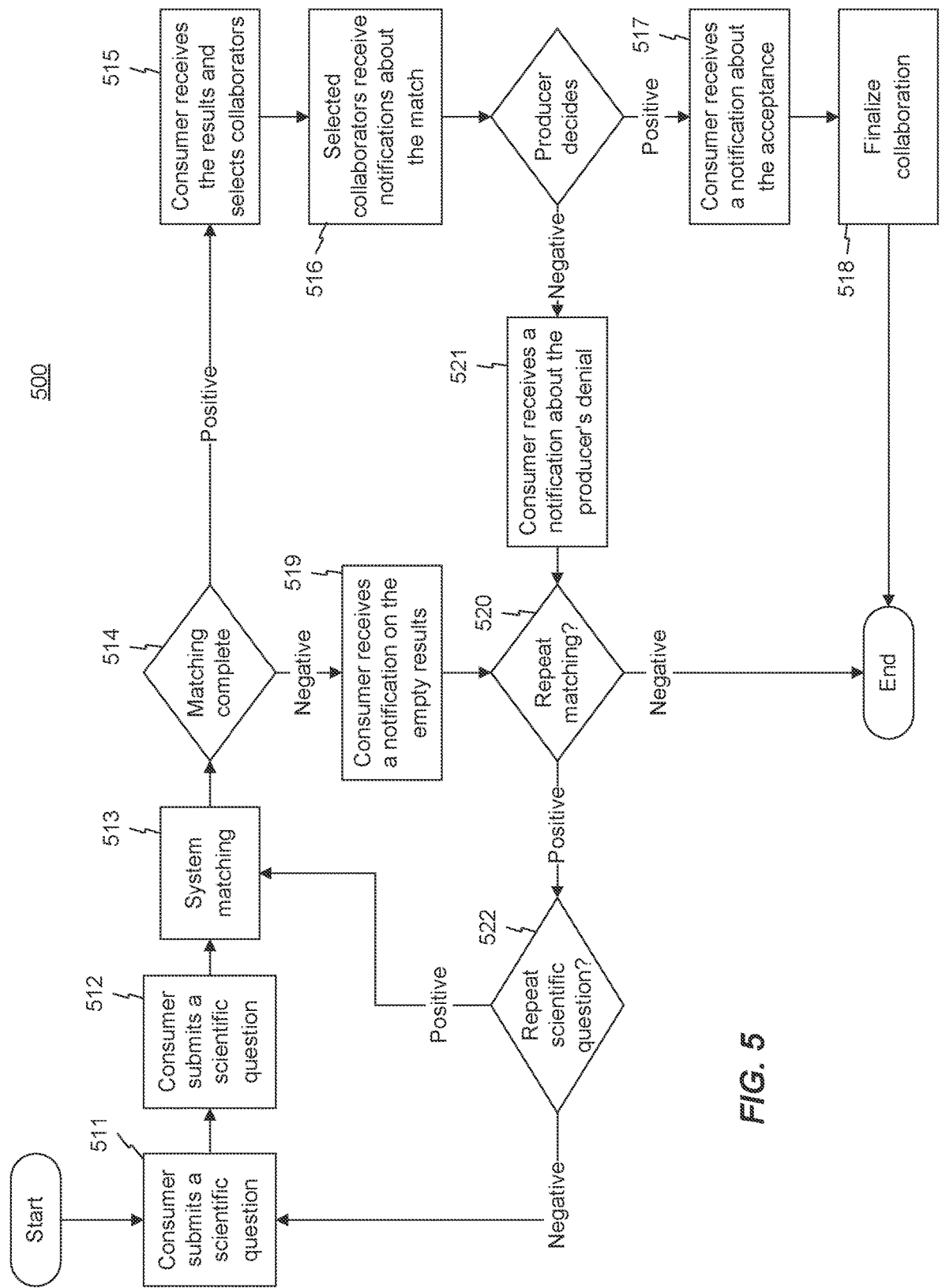
FIG. 5 is an exemplary flowchart of a computerized process for matching a user project with collaborators using a scientific question, according to an aspect of the present disclosure.

FIG. 5 is an exemplary flowchart a computerized process 500 for matching a user project with potential collaborators 130 using a scientific question submitted by consumer 120. The steps depicted in FIG. 5 may be substantially similar to those depicted in FIG. 4, since the steps after identifying potential collaborators 130 remain the same regardless of whether the search query submitted by consumer 120 includes a scientific question or a set of parameters.

Process 500 may begin, in some embodiments, at step 511 where consumer 120 may submit a scientific question. In step 512, the scientific question may be transformed into a user project. As shown in FIG. 6, in the process of translating the scientific question into a project, some of the fields may be inferred thru use of stored logic. For example, in the question "What is the risk of patients having atherosclerotic cardiovascular disease?," it may be inferred that such factors as whether the patient is a smoker, hypertensive, or diabetic may be important. Other factors such as age, race, and gender may be important risk factors. It may also be inferred that certain measurements such as systolic Blood pressure, total cholesterol, LDL, and HDL may be measurements important to the study. Other aspects of the project may also be inferred from the question, such as disease area (e.g. neuroscience, cardiovascular), targeted enzyme or protein (e.g. PCSK-9), drug class (Statin, sIRNA), methods for analysis (e.g. latent class mixed modeling, K-means clustering), and the like.

The inferences may be made, at least initially, on stored data input by someone with scientific knowledge. Inferences may be determined based on one or more datasets. Inferences also may be determined or updated based on insights generated from use of the platform.

Steps 514-521 may be substantially similar to steps 413-420 as they are directed to the functions of collaboration module 240, which are independent from how search and graph module 230 identified the potential collaborators. In some embodiments, however, search and graph module 230 may present an option to consumer 120, at step 520, asking whether he or she wishes to repeat the matching, and at step 521, asking whether he or she wishes to use the same scientific question. Search and graph module 230 may then repeat the matching, at step 513, in response to a positive indication from consumer 120 or prompt for a new scientific question, at step 511, in response to a negative indication.

Alternatively or additionally, producer 110 may also be able to initiate the matching via search and graph module 230 instead of consumer 120. In this case, steps 414-420 or 514-522 may be modified so that producer 110 is the one initially selecting collaborators at step 414 (or step 515) and receiving notifications at steps 416 and 418-420 (or steps 517 and 519-522) instead of consumer 120. Potential collaborators 130 and selected collaborators 140, in this case, may include other producers 110 as well as consumers 120.

Figure 6:
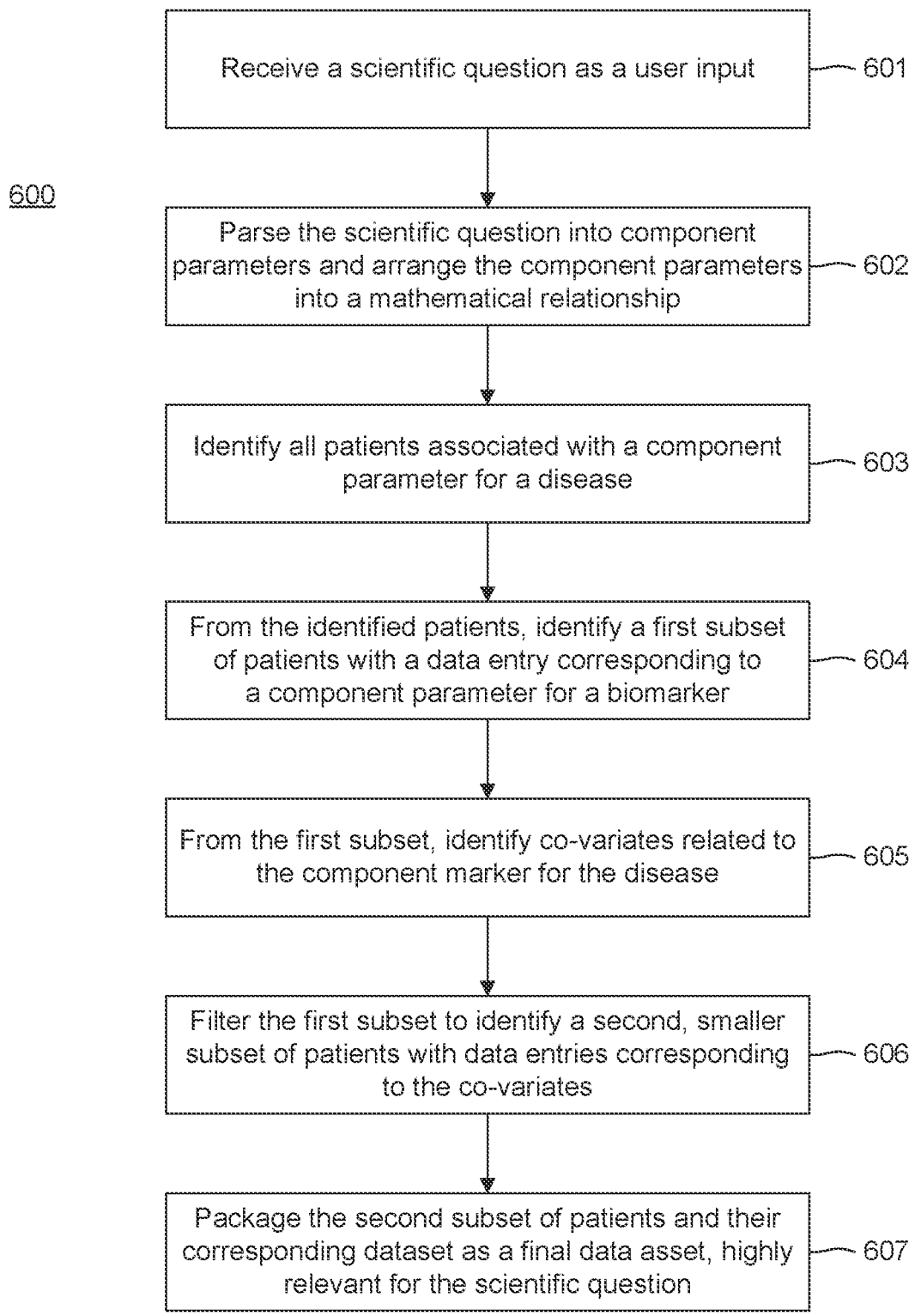
FIG. 6 is an exemplary flowchart of a computerized process for identifying data assets using a scientific question.

FIG. 6 is an exemplary flowchart of a computerized process 600 for identifying data assets 150 using a scientific question submitted by consumer 120. In some embodiments, process 600 may correspond to a portion of steps 511-513, where a scientific question is transformed into a user project and matched with data assets 150. Process 600 may be performed by collaboration platform 200 using different components thereof discussed above.

Process 600 may begin, in some embodiments, at step 601, by receiving a scientific question text as a user input. This scientific question, as was the case in step 512 above, may be in natural language text, as if consumer 120 was asking a question to another person. For example, a scientific question may read "does Lipoprotein (a) level correlate with age of onset of coronary artery disease?" This exemplary scientific question will be used throughout the following description of process 600, but the question itself; any of the words or meanings conveyed therein; or any of the following interpretations, data, or particular explanations are not intended to be limiting in anyway.

At step 602, collaboration platform 200 may parse the scientific question into component parameters and arrange the component parameters into a mathematical relationship. Collaboration platform 200 may use any of the natural language processing techniques available to breakdown the scientific question into words and determine their significance. For example, collaboration platform 200 may breakdown the exemplary scientific question provided above into "lipoprotein (a)," "correlate," "age of onset," and "coronary artery disease"; and recognize that the words describe component parameters "biomarker," "association," "medical history," and "disease," respectively.

In some embodiments, collaboration platform 200 may utilize additional logic in order to recognize common variations of words or terms of arts. In further embodiments, collaboration platform 200 may also recognize and assign values for additional component parameters that may be helpful for transforming the scientific question into a user project and/or complete a project template such as the one shown in FIG. 3. For example, collaboration platform 200 may recognize that the exemplary scientific question also indicates that a component parameter "disease area" can take the value of "cardiovascular" based on the disease "coronary artery disease" identified above. Other component parameters, such as the attributes found in FIG. 3, may also be available for identification and consideration under process 600.

Further, collaboration platform 200 may use the natural language processing techniques to arrange the component parameters into a mathematical expression. For example, collaboration platform 200 may recognize that the component parameters of the exemplary scientific question can be arranged into the expression:

$$A(X, Y, \text{Patients with } Z) > 0$$

where A is an association function, X is the biomarker, Y is the medical history, and Z is the disease. The expression here indicates that the correlation among X, Y, and patients with Z is greater than 0 (i.e., there is a positive correlation among the three variables).

At step 603, collaboration platform 200 may begin by identifying all patients in data assets 150 associated with the component parameter for disease Z. This search may include any entry in data assets 150 where the disease appeared in diagnosis, medical history, and/or adverse events. In some embodiments, collaboration platform 200 may use external knowledge bases, such as the Medical Dictionary for Regulatory Activities (MedDRA) or other public dictionaries, to expand the search to relevant diseases or related medical procedures. For example, a search for disease Z (coronary artery disease) identified above may be expanded to include other diseases such as myocardial infarction, non-fatal stroke, ischemic stroke, cardiovascular death, angina pectoris, transient ischemic attack, etc.; as well as related medical procedures such as coronary angioplasty and stent implantation, thrombolytic therapy, coronary artery bypass graft surgery (CABG), artificial pacemaker surgery, heart valve surgery, etc. At the end of step 603, collaboration platform 200 may temporarily store all patients identified at step 603 as a cohort of interest, and their associated data as a dataset of interest.

For the identified patients, at step 604, collaboration platform 200 may identify a first subset of patients who belong to the cohort of interest and have a record of a particular component parameter. For example, collaboration platform 200 may search the dataset of interest for any patient having a measurement for lipoprotein (a), the biomarker specified in the exemplary scientific question above. In some embodiments, collaboration platform 200 may also determine whether the biomarker is correlated to other biomarkers or genetic mutations, and expand the search to further identify patients where a measurement of the biomarker can be inferred based on the patient's record on the other biomarkers or genetic mutations. At the end of step 604, collaboration platform 200 may update the cohort of interest and the dataset of interest to remove any patients and corresponding data that doesn't fit the criteria discussed herein.

From the first subset of patients, at step 605, collaboration platform 200 may identify co-variates related to the component marker for the disease. In some embodiments, collaboration platform 200 may parse through scientific literatures using natural language processing techniques to identify co-variates that researchers have found to be associated with the particular disease. For example, co-variates for the coronary artery disease may include one or more of: age, gender, race, smoking history/status, body mass index (BMI), blood pressure, LDL, and type 2 diabetes.

Additionally or alternatively, collaboration platform 200 may search data assets 150 and previous user projects in the database to find if any collaborators using collaboration platform 200 have already identified a co-variate. In some embodiments, collaboration platform 200 may use machine learning based on uses, sources and strengths of signal to discard one or more of the identified co-variates. For example, only those with the highest degree of confidence may be kept and the rest discarded.

Using these co-variates, at step 606, collaboration platform 200 may filter the first subset (i.e., the updated cohort of interest) to identify a second, smaller subset of patients with data entries corresponding to the co-variates. This step may be similar to step 604, except the data to search for in the patient records (i.e., dataset of interest) is the co-variates identified at step 605.

Then at step 607, collaboration platform 200 may update the cohort of interest and the dataset of interest to discard any patient that doesn't contain data for the co-variates, thus keeping only those identified as the second subset. In some embodiments, patients belonging to data asset 150 that is inaccessible to consumer 120 may be discarded also. The collaboration platform 200 may then package the resulting dataset of interest as a final data asset, highly relevant for the scientific question.

In some embodiments, this final data asset may then be presented to consumer 120 in the form of a list of different potential collaborators 130 for consumer 120 to select. Collaboration platform 200 may then proceed to connecting consumer 120 to selected collaborators 140, as discussed above with respect to FIGS. 4 and 5. In further embodiments, collaboration platform 200 may also package the scientific question inputted at step 601, the component parameters identified at step 602, and final data asset generated at step 607 into a user project, where the component parameters are converted into attributes.

At any time during process 600, collaboration platform 200 may terminate process 600 if the number of patients in the cohort of interest falls below a predetermined threshold. The predetermined threshold may be the minimum number of data points (i.e., patients) required to answer the scientific question with statistical significance. The predetermined threshold may be set by a user or consumer 120, or it may be determined by collaboration platform 200 using machine learning based on similar scientific questions in related disease area.

Figure 7:
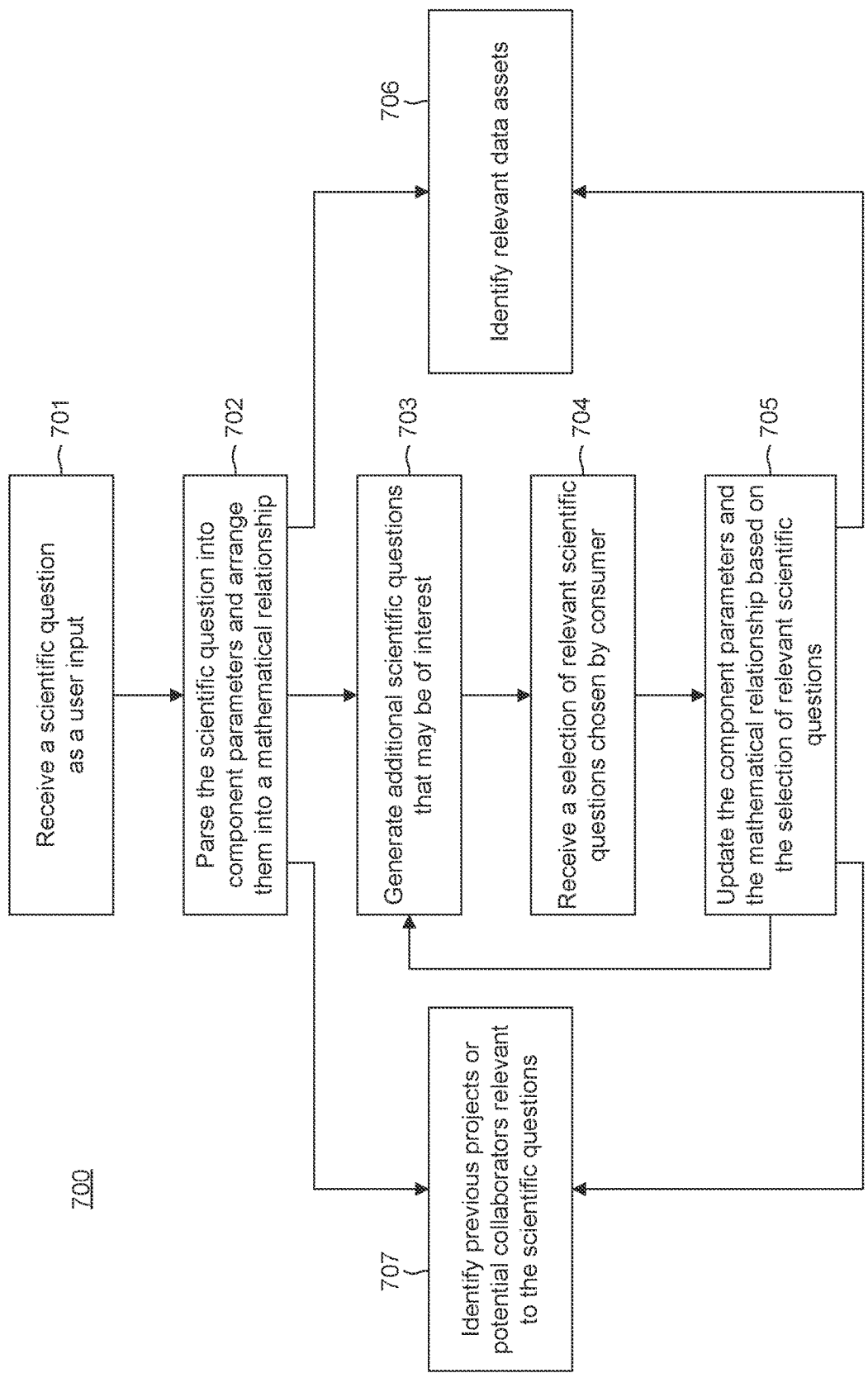
FIG. 7 is an exemplary flowchart of a computerized process for identifying previous projects, potential collaborators, or additional scientific questions using a scientific question.

FIG. 7 is an exemplary flowchart of a computerized process 700 for identifying previous projects, potential collaborators 130, or additional scientific questions using a scientific question submitted by consumer 120. Process 700 may be performed by collaboration platform 200 using different components thereof discussed above. In some embodiments, process 700 may correspond to a portion of steps 511-514, where a scientific question is matched with potential collaborators 130.

Process 700 may begin, in some embodiments, at step 701, by receiving a scientific question in natural language text as a user input and, at step 702, by parsing the scientific question into component parameters and expressing in mathematical relationship. Steps 701 and 702 may be substantially similar to steps 601 and 602 described above.

At step 703, collaboration platform 200 may use machine learning algorithms to generate additional scientific questions that may be of interest. In some embodiments, this may include using the identified component parameters to identify other scientific questions previously submitted by other consumers 120. The other scientific questions identified here may include component parameters similar to those identified for the originally inputted scientific question. Collaboration platform 200 may then create a list of highly relevant scientific questions based on overlap of corresponding dataset of interest, or feedbacks from users received by, for example, insight application 241.

At step 704, collaboration platform 200 may provide the list of highly relevant scientific questions to consumer 120 and receive a selection of relevant scientific questions chosen by consumer 120. In other embodiments, collaboration platform 200 may select a predetermined number of most relevant scientific questions instead of or in addition to user input. For example, an alternative scientific question for the exemplary scientific question received for process 600 above may include: "Does lipoprotein (a) level correlate with age of onset of coronary artery disease, in patients with Alzheimer's."

At step 705, collaboration platform 200 may update the component parameters and the mathematical relationship based on the selection of relevant scientific questions. Additional sets of component parameters and corresponding mathematical relationships may be generated to account for the selected scientific questions. For example, the component parameter for disease, identified as "coronary artery disease" above at step 602 (and thus 702), may be updated to include "coronary artery disease AND Alzheimer's" at step 705. Other component parameters automatically identified by collaboration platform 200, such as the one for disease area, may be updated to include: "cardiovascular, neuroscience" as well.

From both steps 702 and 705, collaboration platform 200 may proceed to either steps 706 and/or 707. At step 706, collaboration platform 200 may identify relevant data assets 150, much like steps 603-607 discussed above. Here, multiple data assets 150 may be identified, each based on different sets of component parameters identified or updated at steps 702 and 705.

At step 707, collaboration platform 200 may identify previous projects or potential collaborators 130 relevant to the scientific questions (i.e., the originally inputted scientific question and/or relevant scientific questions). For example, collaboration platform 200 may look through record of completed user projects or scientific questions that contain similar sets of component parameters. The parties that participated in the identified user projects here may also be identified as potential collaborators 130. In some embodiments, collaboration platform 200 may identify potential collaborators 130 by also searching through user profiles of producers 110 and consumers 120 for similar sets of component parameters. The user profiles may comprise profiles stored in collaboration platform, online publication database of authors, and/or other public and private profiles such as LinkedIn profiles.

In some embodiments, collaboration platform 200 may also share a list of user projects and potential collaborators 130 so identified with consumer 120 if consumer 120 or producer 110 of the identified user projects permit such sharing. This function may be similar to step 515 of FIG. 5 discussed above. As also discussed above at step 515, consumer 120 that received the list of user projects and potential collaborators 130 may then select collaborators (i.e., selected collaborator(s) 140) and/or user projects, and proceed to the next steps for collaborating. In some embodiments, collaboration platform 200 may provide consumer 120 a list of data assets 150 identified at step 706 above, in response to which consumer 120 may select desired data assets 150 and purchase or acquire access thereto.

In some embodiments, collaboration platform 200 may repeat steps 703-705 multiple times as requested by consumer 120 or until no new relevant scientific question is selected. These steps may allow collaboration platform 200 to automatically enrich consumers' 120 queries, thus providing ideas for future research topics or ways to refine their scientific questions.

While the present disclosure has been shown and described with reference to particular embodiments thereof, it will be understood that the present disclosure can be practiced, without modification, in other environments. The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, or other optical drive media.

Computer programs based on the written description and disclosed methods are within the skill of an experienced developer. Various programs or program modules can be created using any of the techniques known to one skilled in the art or can be designed in connection with existing software. For example, program sections or program modules can be designed in or by means of .Net Framework™, .Net Compact Framework™ (and related languages, such as Visual Basic™, C, etc.), Java™, C++, Objective-C™, HyperText Markup Language (HTML), Extensible Markup Language (XML), HTML/Asynchronous JavaScript and XML (AJAX) combinations, or HTML with included Java™ applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A platform for enabling collaboration on analysis of life sciences data across disparate databases for drug discovery and development, the platform comprising at least one hardware processor, at least one memory, and at least one communications means operatively connected to at least one data asset, the at least one memory comprising instructions that, when executed by the at least one hardware processor, cause the platform to perform operations of modules comprising:

a search and graph module for:
generating a user project, wherein the user project comprises multiple attributes determined from one or more of a) system recommendations based on popularity; b) search terms, filters and/or indications of choices from one or more dropdown menus; and c) at least one scientific question in a natural language entered by the user, wherein the multiple attributes comprise static and dynamic elements configured to form new relationships among the static and dynamic elements of the user project or with attributes of one or more producer projects, the one or more producer projects comprising one or more previously generated user projects;
determining one or more matching data assets based on the user project and the one or more producer projects, wherein data assets comprise measurements or observations produced as a result of scientific efforts in the one or more producer projects; and
determining one or more potential collaborators based on the one or more matching data assets, wherein at least a portion of the data assets is previously unshared with one of more of the potential collaborators;

a collaboration module for coordinating a collaboration between the user and one or more selected collaborators associated with one or more selected data assets selected by the user, the selected collaborators being a subset of the potential collaborators and the selected data assets being a subset of the matching data assets, wherein coordinating the collaboration comprises:
notifying the selected collaborators associated with the one or more selected data assets;
providing the selected collaborators with an abstract of the user project;
providing the user with ability to inspect the one or more selected data assets; and
finalizing the collaboration between the user and the selected collaborators, if the user and the one or more selected collaborators assent;

a data management module for:
receiving a schema for each of the one or more producer projects;
receiving data from the one or more selected data assets;
ingesting the received data using common standards and an ontology;
controlling access to at least a portion of the data assets that may be shared with one or more of the potential collaborators,
wherein the ingested data is stored with the one or more producer projects for comparison to the user project by the search and graph module using the multiple attributes; and
an insight application module for generating disease specific inferences relating to the scientific question using the ingested received data, and receiving a feedback from the user and/or the selected collaborators to improve the search and graph module.

2. The platform of claim 1, wherein the scientific question in the natural language is parsed into additional attributes of the user project based on the ontology.

3. The platform of claim 1, wherein the one or more producer projects that most closely match the user project are displayed in a ranked order, wherein the projects are ranked based on one or more of:
a number of matching attributes;
most popular data assets selected in the past by previous users; or
a scientific question type.

4. The platform of claim 1, wherein determining and displaying the matching data assets and the potential collaborators further comprise:
identifying the one or more producer projects that most closely match the user project,
wherein the user project and the one or more producer projects each further comprise additional attributes including producers, a disease type, a disease classification, linked projects, drugs, or trials, and/or data assets.

5. The platform of claim 1, wherein the search and graph module further comprises:
a quantitative matching module configured to determine the matching data assets or the potential collaborators based on one or more schema defined by the user project;
a qualitative matching module configured to identify the matching data assets or the potential collaborators using the attributes of the user project; and
a recommendation module configured to output an optimized combination of the matching data assets and the potential collaborators identified by the quantitative matching module and/or the qualitative matching module.

6. The platform of claim 1, wherein the selected collaborators further comprise a subset of the potential collaborators associated with analytical models or research groups.

7. The platform of claim 1, wherein finalizing the collaboration further comprises:
generating one or more contracts among the user and the selected collaborators;
obtaining indications of assent from each of the user and the selected collaborators; and
exchanging electronic payments among the user and the selected collaborators according to the contracts.

8. The platform of claim 1, wherein ingesting the received data using the common standards and the ontology further comprises:
parsing the received data to identify data elements with known tags or indices;

harmonizing a first set of the data elements by transforming the data elements to standard data types based on the ontology;

normalizing a second set of the data elements to standard units and updating the data assets to reflect the normalization; and making the ingested received data available on the platform for concurrent access.

9. The platform of claim 8, wherein ingesting the received data using the common standards and the ontology further comprises:

performing health checks on the received data by comparing the data elements to known safety ranges associated with the known tags or indices.

10. The platform of claim 1, wherein ingesting the received data using the common standards and the ontology further comprises:

organizing the received data based on a set of knowledge base templates associated with the ontology; and making logical combinations of the received data to form one or more useable packages that match the user project.

11. The platform of claim 1, wherein ingesting the received data using the common standards and the ontology further comprises:

anonymizing the received data by assigning a unique global identifier for each group of data elements; and reorganizing the received data across the selected data assets based on the assigned unique global identifiers.

12. The platform of claim 1, wherein the received data have been collected from lab exams, medical records, or clinical trials.

13. A method for enabling collaboration on data analysis of life sciences data across multiple disparate databases for performing exploratory analysis for drug discovery and development, the method comprising:

generating a user project, wherein the user project comprises multiple attributes determined from a) a user's profile; b) the user's past activities; c) system recommendations based on popularity; d) search terms, filters and/or indications of choices from one or more drop-down menus; and/or e) at least one scientific question in a natural language entered by the user, wherein the multiple attributes comprise static and dynamic elements configured to form new relationships among the static and dynamic elements of the user project or with attributes of one or more producer projects, the one or more producer projects comprising one or more previously generated user projects;

determining one or more matching data assets based on the user project and the one or more producer projects, wherein data assets comprise measurements or observations produced as a result of scientific efforts in the one or more producer projects;

determining one or more potential collaborators based on the one or more matching data assets, wherein at least a portion of the data assets is previously unshared with one of more of the potential collaborators;

coordinating a collaboration between the user and one or more selected collaborators associated with one or more selected data assets selected by the user, the selected collaborators being a subset of the potential collaborators and the selected data assets being a subset of the matching data assets;

notifying the selected collaborators associated with the one or more selected data assets;

providing the selected collaborators with an abstract of the user project;

providing the user with ability to inspect the one or more selected data assets;

finalizing the collaboration between the user and the selected collaborators, if the user and the one or more selected collaborators assent;

receiving a schema for each of the one or more producer projects;

receiving data from the one or more selected data assets;

ingesting the received data using common standards and an ontology;

controlling access to at least a portion of the data assets that may be shared with one or more of the potential collaborators, wherein the ingested data is stored with the one or more producer projects for comparison to the user project by the search and graph module using the multiple attributes;

generating disease specific inferences relating to the scientific question using the ingested received data; and receiving a feedback from the user and/or the selected collaborators to improve the exploratory analysis.

14. The method of claim 13, further comprising:

displaying the one or more producer projects that most closely match the user project in a ranked order, wherein the projects are ranked based on one or more of:

a number of matching attributes;

most popular data assets selected in the past by previous users; or a scientific question type.

15. The method of claim 13, wherein determining and displaying the matching data assets and the potential collaborators further comprise:

identifying the one or more producer projects that most closely match the user project, wherein the user project and the one or more producer projects each further comprise additional attributes including producers, a disease type, a disease classification, linked projects, drugs, or trials, and/or data assets.

16. The method of claim 13, further comprising:

determining the matching data assets or the potential collaborators based on one or more schema defined by the user project;

identifying the matching data assets or the potential collaborators using the attributes of the user project; and outputting an optimized combination of the matching data assets and the potential collaborators.

17. The method of claim 13, wherein the selected collaborators further comprise a subset of the potential collaborators associated with analytics modules or research groups.

18. The method of claim 13, further comprising:

generating one or more contracts among the user and the selected collaborators;

obtaining indications of assent from each of the user and the selected collaborators; and exchanging electronic payments among the user and the selected collaborators according to the contracts.

19. The method of claim 13, wherein ingesting the received data using the common standards and the ontology further comprises:

parsing the received data to identify data elements with known tags or indices;

harmonizing a first set of the data elements by transforming the data elements to standard data types based on the ontology;

normalizing a second set of the data elements to standard units and updating the data assets to reflect the normalization; and making the ingested received data available on the platform for concurrent access.

20. The method of claim 19, wherein ingesting the received data using the common standards and the ontology further comprises:

performing health checks on the received data by comparing the data elements to known safety ranges associated with the known tags or indices.

21. The method of claim 13, wherein ingesting the received data using the common standards and the ontology further comprises:

organizing the received data based on a set of knowledge base templates associated with the ontology; and making logical combinations of the received data to form one or more useable packages that match the user project.

22. The method of claim 13, wherein ingesting the received data using the common standards and the ontology further comprises:

anonymizing the received data by assigning a unique global identifier for each group of data elements; and reorganizing the received data across the selected data assets based on the assigned unique global identifiers.

23. The method of claim 13, wherein the received data have been collected from lab exams, medical records, or clinical trials.

24. The platform of claim 1, wherein the one or more matching data assets is determined further based on one or more schema defined by the user project, the one or more schema representing organizational structures of the matching data assets that adapt to new data assets.

25. The method of claim 13, wherein the scientific question in the natural language is parsed into additional attributes of the user project based on the ontology.

26. The method of claim 13, wherein the one or more matching data assets is determined further based on one or more schema defined by the user project, the one or more schema representing organizational structures of the matching data assets that adapt to new data assets.

* * * * *